(12) United States Patent
Leyns et al.

(10) Patent No.: US 8,215,491 B2
(45) Date of Patent: Jul. 10, 2012

(54) EVALUATION OF PARTICULATE MATERIAL

(75) Inventors: Frederik Leyns, Oosterzele (BE); Willy Dillen, Sint-Amandsberg (BE); Marcin Olik, Kortrijk (BE)

(73) Assignee: CropDesign N.V., Ghent (BE)

( * ) Notice: Subject to any disclaimer, the term of this patent is extended or adjusted under 35 U.S.C. 154(b) by 507 days.

(21) Appl. No.: 12/148,623

(22) Filed: Apr. 21, 2008

(65) Prior Publication Data

US 2008/0197057 A1    Aug. 21, 2008

Related U.S. Application Data

(63) Continuation of application No. 10/740,029, filed on Dec. 18, 2003, now Pat. No. 7,367,458.

(30) Foreign Application Priority Data

Dec. 18, 2002    (EP) .................................... 02080446

(51) Int. Cl.
*B07C 5/16*    (2006.01)
(52) U.S. Cl. ......................... 209/645; 209/134; 209/135
(58) Field of Classification Search .................. 209/134, 209/135, 551; 47/14, 581 R; 177/71
See application file for complete search history.

(56) References Cited

U.S. PATENT DOCUMENTS

| | | | |
|---|---|---|---|
| 4,391,338 A | 7/1983 | Patashnick et al. | |
| 4,558,091 A | 12/1985 | Hubbard | |
| 4,588,091 A * | 5/1986 | Wade | 209/546 |
| 4,865,627 A * | 9/1989 | Dewitz et al. | 95/12 |
| 5,294,002 A * | 3/1994 | Moses | 209/135 |
| 5,949,001 A * | 9/1999 | Willeke | 73/865.5 |
| 6,213,307 B1 * | 4/2001 | Stein | 209/139.1 |
| 6,651,480 B2 * | 11/2003 | Rupprecht et al. | 73/1.34 |
| 7,367,458 B2 * | 5/2008 | Leyns et al. | 209/551 |
| 2002/0122177 A1 | 9/2002 | Sioutas et al. | |
| 2002/0144458 A1 * | 10/2002 | Hunter et al. | 47/14 |

FOREIGN PATENT DOCUMENTS

| | | |
|---|---|---|
| DE | 40 41 994 | 7/1992 |
| GB | 617276 | 2/1949 |
| GB | 1 378 715 | 2/1972 |

* cited by examiner

*Primary Examiner* — Terrell Matthews
(74) *Attorney, Agent, or Firm* — Ann R. Pokalsky, Esq.; Dilworth & Barrese, LLP

(57) ABSTRACT

The invention provides apparatus for determining and recording characteristics of particulate material in a batch of such material comprising a separator chamber having an inlet, means for reading an identifier on a batch of particulate material supplied to the inlet and providing the identifier as a digital output, means for causing a flow of gas in the separator chamber to separate the particulate material into a first fraction and a second fraction, first counting means, second counting means, means for weighing the first fraction and providing the result as a digital output, and means for integrating the digital outputs and for transferring them to a computer programmed to store data in prescribed format in a database, from which it may be manipulated to afford comparison of characteristics of batches of particulate material.

6 Claims, 2 Drawing Sheets

EVALUATION OF PARTICULATE MATERIAL

This application is a continuation application of U.S. Ser. No. 10/740,029, filed Dec. 18, 2003, now U.S. Pat. No. 7,367,458.

This invention relates to evaluation of particulate material and is especially concerned with evaluation of seed in a batch of plant product.

In breeding of plants cultivated for their seeds. (also called seed crops) for example—rice, wheat, barley, corn, soybean, canola, sunflower, millet and safflower, a major goal is to find genotypes that have a high seed yield. Breeders often have to analyse the seed yield of large populations of plants with different genotypes, obtained for example through sexual crossing of parental lines. Molecular breeders, who create variability by insertion of transgenes in a plant species, also have to cope with large plant populations of which the seed yield needs to be assessed. Tools for fast, accurate and efficient measurement of seed yield are a necessity for the plant breeding industry.

It is one practice to evaluate seed produced by plants by a procedure which involves several steps. The seeds are physically separated from the plant, the harvest step, and then cleaned to remove non-seed remnants originating from the maternal plant and dust or other contaminating particles. Mature seeds are discriminated from improperly matured seeds (hereinafter "immature seeds"), e.g. seeds that are not completely filled. In most cases the ratio of mature seeds versus immature seeds is recorded as a parameter that is relevant for the breeders. The mature seeds are weighed and counted, so that the total mature seed weight (otherwise referred to as the yield) which is an important parameter for breeders, can be derived as well as the average weight per mature seed which gives a value for comparison with for example, the thousand kernel weight that is commonly used as an important parameter by breeders.

Instruments used for conducting these measurements in such a procedure include balances for measuring seed weight and seed counters for counting the number of seeds, all of which exist in different commercially available types. One type of seed counter comprises an inlet for a batch of seed, a system that allows the seeds to drop one by one, and a system to detect each particle of a defined size that passes in front of an optical detector. Instruments for cleaning the seeds also exist in different commercially available types. Some are based on the passage of seeds over sets of shaking sieves with different mesh size, until seeds of the right particle size are retained on one of those sieves. Other instruments are based on the differential aerodynamic and/or gravity properties of seeds versus contaminants in a fluid flow, usually a stream of air. Discrimination of matured versus immature seeds can also be done based on the principle of differential aerodynamic/gravity properties.

It is one object of the present invention to provide improved apparatus for the evaluation of particulate material in a batch of such material.

It is another of the objects of this invention to provide an improved process for the evaluation of mature seeds in a batch of plant product.

The invention provides in one of its aspects apparatus for determining and recording characteristics of particulate material in a batch of such material comprising a separator chamber having an inlet through which a batch of particulate material may be supplied to the separator chamber, means for reading an identifier on the batch of particulate material supplied to the inlet and providing the identifier as a digital output, means for causing a flow of gas in the separator chamber to separate the particulate material into a first fraction consisting essentially of particulate material having desired characteristics and a second fraction consisting essentially of particulate material not having the desired characteristics, first counting means for counting the particles in the first fraction and providing the result as a digital output, second counting means for counting particles of the particulate material in the batch or for counting particles of particulate material in the second fraction and providing the result as a digital output, means for weighing the first fraction and providing the result as a digital output, and means for integrating the digital outputs and for transferring them to a computer programmed to store data in prescribed format in a database from which it may be manipulated to afford comparison of characteristics of batches of particulate material.

The word "comprising" where used herein is intended to encompass the notion of "including" and the notion of "consisting essentially of".

Apparatus according to the invention is preferably constructed and arranged so that the inlet to the separator chamber, an outlet from the separator chamber for the first fraction, counter means and means for weighing the first fraction are arranged one above another so that the first fraction may be allowed to fall from the inlet to the weighing means. Preferably, the apparatus is so constructed and arranged that particles may drop one by one from the inlet into the separator chamber. Preferably the first fraction follows an at least substantially linear line of passage from the inlet to the weighing means. In one embodiment hereinafter described the particulate material is allowed to fall through a vertically disposed passageway shaped to disrupt the falling particulate material as it reaches an entry port through which flow of gas may enter the separator chamber.

The means for causing a flow of gas in the separator chamber of apparatus according to the invention may take any suitable form for example a compressed gas supply may be utilised to blow the gas though the chamber, or fan means may be utilised to draw the gas through the chamber. The gas used is preferably air, in which case the fan means is preferred. Preferably, the gas is caused to flow in the separator chamber at least somewhat across the line of passage of particulate material supplied to the separator chamber, whereby particles are borne to a lesser or greater degree from the line of passage. Preferably baffle means is provided within the separator chamber at a position from the line of passage commensurate with restraining particles of the second fraction from returning to the first fraction after separation. The separator chamber may include a chamber in which the second fraction is retained or alternatively may have a discharge opening through which the second fraction is evacuated from the separating chamber.

Preferably, the separator chamber is provided with a vent through which material such as dust or other plant residue may be evacuated from the separator chamber.

In apparatus according to the invention, the means for reading an identifier on the batch is preferably a bar code reader but may be any other suitable reader appropriate to the identifier employed.

In apparatus according to the invention, the particles of particulate material are allowed or caused to drop one by one through the first and second counter means so they may be counted. Any counting means capable of detecting the particles may be employed for example optical or capacitance counters. We prefer to employ optical counting means or by capacitance counting.

Apparatus according to the invention may also comprise means for optical assessment of grain size of particles in the first fraction.

Apparatus according to the invention may also comprise means for applying the identifier to the batch of particulate material.

In apparatus according to the invention, the means for reading the identifier, the first and second counting means and the means for weighing the first fraction each provide output in digital form. These are preferably integrated by use of software in a computer device and fed therefrom to the database. The database may be manipulated to inspect and compare data to determine various characteristics such as the amount of particles in the first fraction, the average weight of particles in the first fraction and the ratio of particles in the first fraction to the number of particles in the second fraction.

Apparatus according to the invention permits derivation of data about the particulate material without human intervention other than perhaps initial feeding of the particulate material to the inlet and/or removal of particles from the apparatus. It may be used for a variety of purposes and is especially useful for evaluation of mature seeds in a batch of material obtained by harvesting one or more plants. In such use, the apparatus provides an integrated automatic process for separating seed in a batch harvested from one or more plants from detritus, and separating matured seed from immature seed. By use of the apparatus one may derive in a single operation desired data about key parameters of interest to the plant breeder such as seed yield, average seed weight and ratio of matured to immature seed in the batch.

The invention provides in another of its aspects a process for evaluating and recording characteristics of seed in a batch of plant product comprising the steps of identifying the batch, automatically transferring the batch to means for separating the seed to provide a first fraction consisting essentially of mature seeds and a second fraction consisting essentially of immature seeds, to means for counting the seeds in such manner that the number of seeds in each fraction is determined and to means for weighing the first fraction of seeds, determining the average weight of the seeds in the first fraction, manipulating the results to determine the ratio of mature seeds in the batch to improperly matured seeds in the batch and recording results in a prescribed format in a computer database together with the batch identifier.

The computer database compiled by subjecting batches of plant product to a process as aforesaid may be interrogated and enables rapid comparison of characteristics from a multitude of different plants and thus permits rapid determination of seeds from which further plants may be derived which yield seeds having desired characteristics.

The invention provides in another of its aspects a process for comparing one or more of the characteristics of seed yield, average seed weight and/or ratio of mature versus improperly matured seeds in a batch of plant product with corresponding characteristics of other batches of plant product, in which a computer database compiled by subjecting batches of plant product to a process according to the last preceding paragraph but one is interrogated concerning said one or more characteristics.

In order that the invention may become more clear there now follows a description to be read with the accompanying drawings of three example instruments for use in apparatus according to the invention and their use in a process according to the invention selected for description to illustrate the invention by way of example.

IN THE DRAWINGS

Figure 1:
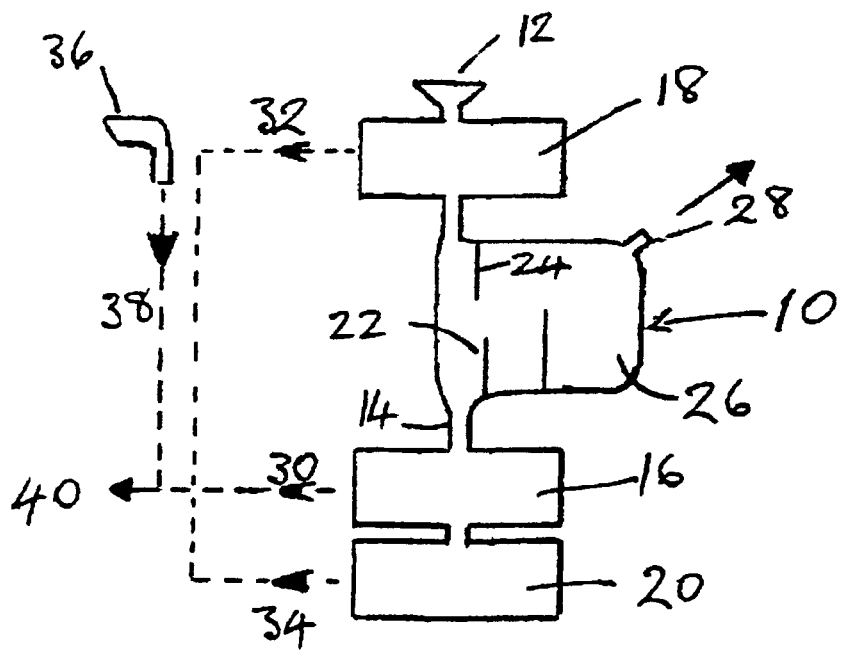
FIG. 1 is a schematic view in section of a first example instrument.
Figure 2:
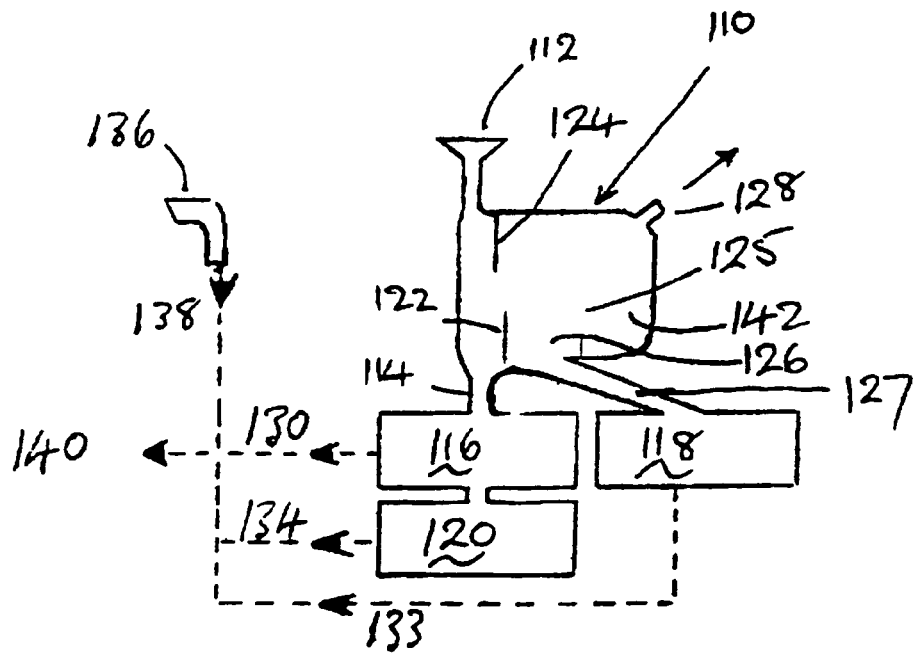
FIG. 2 is a schematic view in section of a second example instrument.

The example instruments provide means for determining and recording characteristics of particulate material in a batch of such material.

The first example instrument comprises a separator chamber (10) having an inlet (12) through which a batch of particulate material may be supplied to the separator chamber, an outlet (14) from the separator, first counter means (16), second counter means (18) and a balance (20). These are arranged one above another. The first counter means has a vibratory feeder device to separate the particulate material into individual particles, so that they pass this and the lower counter one by one.

A fan (not shown) is provided for drawing a flow of air through the separator chamber (10) via the inlet (12) and generally from left to right as viewed in FIG. 1 to separate particulate material passing through the separator chamber into a first fraction consisting essentially of heavier particulate material and a second fraction consisting essentially of lighter material. The instrument is so constructed and arranged that in use, particles may drop one by one past the counter (18), into the separator (10) and so that those of the first fraction may fall from the inlet (12) to the balance (20) in an at least substantially vertical, linear line of passage. The flow of air drawn through the separator chamber is such that particles are borne to a lesser or greater degree from the line of passage. Baffle means in the form of vertically extending metal plates (22, 24) is provided within the separator chamber at a position from the line of passage commensurate with restraining lighter particles from returning to the first fraction after separation. The separator chamber (10) includes a subchamber (26) in which the second fraction is retained. A vent (28) is provided at an upper extremity of the separator chamber through extraneous matter such as dust or plant residue may be evacuated from the separator chamber.

Each of the counters (16 and 18) comprises an optical counting means arranged to count particles falling past it. The first counting means (16) is provided for counting the particles in the first fraction and the second counting means (18) for counting particles of the particulate material in the batch. The counting means provide the results as a digital outputs (30, 32). The balance provides means for weighing the first fraction and also provides its result as a digital output (34).

The instrument has a bar code reader (36) which provides means for reading an identifier in the form of a bar code on the batch of particulate material supplied to the inlet. The bar code reader is arranged to supply the identifier bar code as a digital output (38).

The instrument also comprises means (not shown) for applying the identifier to the batch of particulate material.

The various digital outputs (30, 32, 34, 38) are fed from the instrument to a data collection point (40) at which they are integrated by use of software in a computer device. The information derived is then supplied to a computer programmed to store data in prescribed format in a database from which it may be manipulated to afford comparison of characteristics of batches of particulate material.

The second example instrument comprises a separator chamber (110) having an inlet (112) through which a batch of particulate material may be supplied to the separator chamber, an outlet (114) from the separator, first counter means (116) second counter means (118) and a balance (120). The inlet (112), outlet (114), first counter means (116) and balance (120) are arranged one above another. Fan means (not shown) as employed in the first example instrument is provided for drawing a flow of air through the separator chamber (110) to separate particulate material passing through the separator chamber into a first fraction consisting essentially of heavier particulate material and a second fraction consisting essentially of lighter material. The instrument is so constructed and arranged that in use, particles may drop from the inlet (112) via a vibratory hopper and pass one by one, into the separator chamber (110) and so that those of the first fraction may fall from the inlet (112) to the balance (120) in an at least substantially vertical, linear line of passage. The air flow in the separator chamber serves to carry particles to a lesser or greater degree from the line of passage. Baffle means in the form of vertically extending metal plates (122, 124) is provided within the separator chamber at a position from the line of passage commensurate with restraining lighter particles from returning to the first fraction after separation. The separator chamber (110) includes a sub-chamber (126) defined by the baffle (122) and a wall (125) in which the second fraction is collected. Particles of the second fraction may then pass through a conduit (127) and fall past the second counter (118) and collect in a chamber (not shown). A second sub-chamber (142) defined by the wall (125) and an interior wall portion of the separator chamber, is provided into which a third fraction of the batch may pass. A vent (128) is provided at an upper extremity of the separator chamber through which extraneous matter such as dust may be evacuated from the separator chamber.

Each of the counters (116 and 118) comprises an optical counting means arranged to count particles falling past it. The first counting means (116) is provided for counting the particles in the first fraction and the second counting means (118) for counting particles of the second fraction. The counting means each provide results as a digital output (130, 133).

The balance provides means for weighing the first fraction and also provides its result as a digital output (134).

The instrument has a bar code reader (136) which provides means for reading an identifier in the form of a bar code on the batch of particulate material supplied to the inlet. The bar code reader is arranged to supply the identifier bar code as a digital output (138).

The instrument also comprises means (not shown) for applying the identifier to the batch of particulate material.

The various digital outputs (130, 133, 134, 138) are fed from the instrument to a data collection point (140) at which they are integrated by use of software in a computer device. The information derived is then supplied to a computer programmed to store data in prescribed format in a database from which it may be manipulated to afford comparison of characteristics of batches of particulate material.

Figure 3:
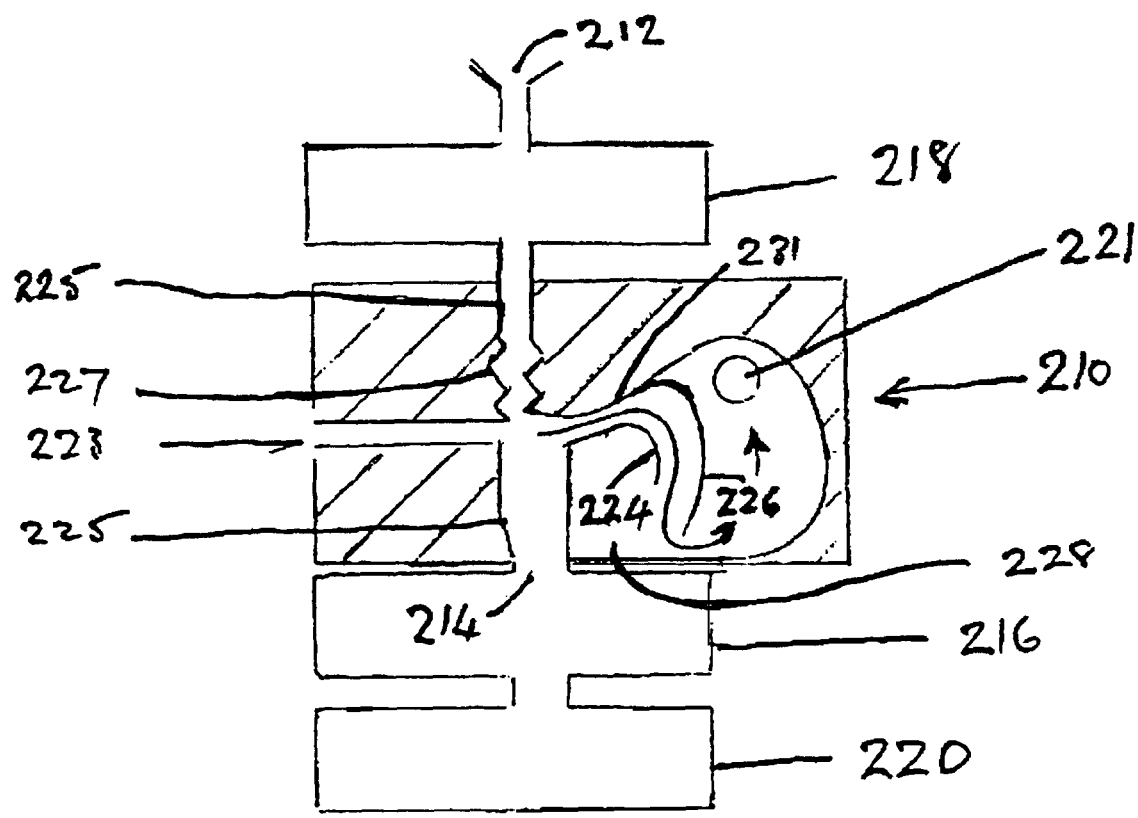
FIG. 3 is a schematic view in section of a third example instrument.

The third example instrument comprises a separator chamber (210) having an inlet (212) through which a batch of particulate material may be supplied via a vibratory hopper (not shown) to the separator chamber, an outlet (214) from the separator chamber, first counter means (216), second counter means (218) and a balance (220). These are arranged one above another. A fan (221) is provided for drawing a flow of air through the separator chamber (210) via an inlet port (223) and generally from left to right as viewed in FIG. 3 to separate particulate material passing through the separator chamber into a first fraction consisting essentially of heavier particulate material and a second fraction consisting essentially of lighter material. In this embodiment the particulate material is allowed to fall through a vertically disposed passageway (225) shaped (227) to disrupt the passage of particles of falling material as they reach the entry port (223) through which flow of gas may enter the separator, being drawn through the separator chamber by the fan (221). Baffles (224, 226) and an internal wall (231) of the separator chamber are curved in such a way that air drawn through the chamber follows a somewhat sinusoidal path to one side of the passageway (225) as indicated by the arrows in FIG. 3.

The instrument is so constructed and arranged that in use, particles may drop one by one past the counter (218), into the separator (210) and so that those of the first fraction may fall from the inlet (212) to the balance (220) in an at least substantially vertical line of passage. The flow of air drawn through the separator chamber is such that particles are borne to a lesser or greater degree from the line of passage. Air flowing between the baffles (224, 226) restrains lighter particles from returning to the first fraction after separation. The separator chamber (210) includes a sub-chamber (228) in which the second fraction is retained. The air drawn out of the separator chamber by the fan (221 carries extraneous matter such as dust through the fan and out of the separator chamber.

Each of the counters (216 and 218) comprises an optical counting means arranged to count particles falling past it. The first counting means (216) is provided for counting the particles in the first fraction and the second counting means (218) for counting particles of the particulate material in the batch. The counting means provide the results as digital outputs (not shown) in the same way as in the first example instrument. The balance provides means for weighing the first fraction and also provides its result as a digital output (not shown) as in the first example instrument.

The instrument has a bar code reader (not shown) which provides means for reading an identifier in the form of a bar code on the batch of particulate material supplied to the inlet. The bar code reader is arranged to supply the identifier bar code as a digital output.

The instrument also comprises means (not shown) for applying the identifier to the batch of particulate material.

As with the first example instrument the various digital outputs are fed from the instrument to a data collection point at which they are integrated by use of software in a computer device. The information derived is then supplied to a computer programmed to store data in prescribed format in a database from which it may be manipulated to afford comparison of characteristics of batches of particulate material.

In a first process according to the invention, the first example instrument was used to determine characteristics of a batch of seed harvested from a plant. The instrument applied a unique bar code to the batch, which was read by the bar code reader (36), which in turn sent its digital output (38) to the data collection point (40) thereby identifying the batch. The batch was automatically transferred seed by seed from the inlet (12) to the separator chamber (10). Air flowing in the separator chamber caused material supplied to the separator chamber to separate into a first fraction consisting essentially of mature seeds and a second fraction consisting essentially of immature seeds and a third fraction consisting of unwanted dust and other plant materials.

The first fraction fell onto the balance where its total weight was measured and transferred as digital output (34). The second fraction was captured in the sub-chamber (26) and the third fraction was emitted from the exhaust (28). Seed falling past the counters (18, 16) was counted by the optical devices and the result supplied as digital outputs (30, 32) to the data collection point.

At the data collection point, the average weight of the seeds in the first fraction was determined and the data manipulated to determine the ratio of mature seeds in the batch to immature seeds in the batch. The results were sent to and recorded in a computer database in a prescribed format together with the batch identifier. The seed yield was derived from the balance output, the average seed weight was derived by taking the ratio of the seed yield to the number of mature seeds as assessed by the output of the first counter (16) and the ratio of mature seeds versus immature seeds is derived by taking the ratio of the output from the first counter (16) to the output from the second counter (18) minus the output of the first counter. Characteristics of seed yield, average seed weight and/or ratio of mature versus immature seeds in the batch were compared with corresponding characteristics of other batches of plant product assembled in the computer database.

In a second process according to the invention, the second example instrument was used to determine characteristics of a batch of seed harvested from a plant. The instrument applied a unique bar code to the batch, which was read by the bar code reader (136), which in turn sent its digital output (138) to the data collection point (140) thereby identifying the batch. The batch was automatically transferred seed by seed from the inlet (112) to the separator chamber (110). Air flowing in the separator chamber caused material supplied to the separator chamber to separate into a first fraction consisting essentially of mature seeds, a second fraction consisting essentially of immature seeds and a third fraction consisting of unwanted dust and other plant materials.

The first fraction fell onto the balance (120) where its total weight was measured and transferred as digital output (134). The second fraction was captured in the sub-chamber (126) and the third fraction was passed into the second sub-chamber from whence dust was exhausted via the exhaust (128). Seed falling past the counters (118, 116) was counted by the optical devices and the result supplied as digital outputs (130, 133) to the data collection point (140).

At the data collection point, the average weight of the seeds in the first fraction was determined and the data manipulated to determine the ratio of mature seeds in the batch to immature seeds in the batch. The results were sent to and recorded in a computer database in a prescribed format together with the batch identifier. The seed yield was derived from the balance output, the average seed weight was derived by taking the ratio of the seed yield to the number of mature seeds as assessed by the output of the first counter (116) and the ratio of mature seeds versus immature seeds was derived by taking the ratio of the output from the first counter (116) to the output from the second counter (118).

In a third process according to the invention, the third example instrument was used in a substantially similar way to the first process to separate particulate material into a first fraction consisting essentially of mature seeds and a second fraction consisting essentially of immature seeds and a third fraction consisting of extraneous materials. As in the first process, the weight of the first fraction was measured and transferred as digital output. The second fraction was captured in the sub-chamber (228) and the third fraction was exhausted through the fan (221). As in the first process, seed falling past the counters (218, 216) was counted by the optical devices and the result supplied as digital outputs to the data collection point.

At the data collection point, the average weight of the seeds in the first fraction was determined and the data manipulated to determine the ratio of mature seeds in the batch to immature seeds in the batch. The results were sent to and recorded in a computer database in a prescribed format together with the batch identifier. The seed yield was derived from the balance output, the average seed weight was derived by taking the ratio of the seed yield to the number of mature seeds as assessed by the output of the first counter and the ratio of mature seeds versus immature seeds is derived by taking the ratio of the output from the first counter to the output from the second counter minus the output of the first counter.

Characteristics of seed yield, average seed weight and/or ratio of mature versus immature seeds in the batch were compared with corresponding characteristics of other batches of plant product assembled in the computer database.

One may select which of the example instruments is used in accordance with the nature of the seeds and of the impurities which depends on the plant species and the harvesting system used. In either case one may compare one or more of the characteristics of seed yield, average seed weight and/or ratio of mature versus immature seeds in a batch of plant product with corresponding characteristics of other batches of plant product, by interrogating the computer database compiled by subjecting many-batches of plant product to a process according to the invention.

The invention claimed is:

1. Apparatus for determining and recording characteristics of particulate material in a batch of such material comprising:
    a separator chamber having an inlet through which a batch of particulate material is supplied to the separator chamber;
    means for reading an identifier on the batch of particulate material supplied to the inlet and providing the identifier as a digital output;
    means for causing a flow of gas in the separator chamber to flow only across a substantially vertical line of passage of particulate material supplied to the separator chamber such that particles are borne to a lesser or greater degree from the vertical line of passage and wherein the flow of gas separates the particulate material into a first fraction consisting essentially of particulate material having desired characteristics and a second fraction consisting essentially of particulate material not having the desired characteristics;
    first counting means for counting the particles in the first fraction and providing the result as a digital output;
    second counting means for counting particles of the particulate material in the batch or for counting particles of particulate material in the second fraction and providing the result as a digital output;
    means for weighing the first fraction and providing the result as digital output; and
    means for integrating the digital outputs and for transferring them to a computer programmed to store data in prescribed format in a database from which it may be manipulated to afford comparison of characteristics of batches of particulate material.

2. An apparatus according to claim 1 wherein the flow of gas further separates the particulate matter into a third fraction consisting of unwanted dust and other plant materials.

3. An apparatus according to claim 1 wherein the flow of gas further separates the particulate matter into a third fraction consisting of extraneous materials.

4. A process for evaluating and recording characteristics of seed in a batch of plant product comprising the steps of:
    identifying the batch;
    automatically transferring the batch to the separator chamber in the apparatus of claim 1 to provide a first fraction consisting essentially of mature seeds, a second fraction consisting essentially of improperly matured seeds and a third fraction consisting of unwanted dust and other plant materials;

automatically transferring the first and second fractions to the means for counting seeds in the apparatus of claim 1 in such manner that the number of seeds in each fraction is determined;

automatically transferring the first fraction to the means for weighing the first fraction of seeds in the apparatus of claim 1;

determining the average weight of the seeds in the first fraction;

manipulating the results to determine the ratio of mature seeds in the batch to immature seeds in the batch; and recording results in a prescribed format in a computer database together with the batch identifier.

5. A process for evaluating and recording characteristics of seed in a batch of plant product comprising the steps of:

identifying the batch;

automatically transferring the batch to the separator chamber in the apparatus of claim 1 to provide a first fraction consisting essentially of mature seeds, a second fraction consisting essentially of improperly matured seeds and a third fraction consisting of extraneous materials;

automatically transferring the first and second fractions to the means for counting seeds in the apparatus of claim 1 in such manner that the number of seeds in each fraction is determined;

automatically transferring the first fraction to the means for weighing the first fraction of seeds in the apparatus of claim 1;

determining the average weight of the seeds in the first fraction;

manipulating the results to determine the ratio of mature seeds in the batch to immature seeds in the batch; and recording results in a prescribed format in a computer database together with the batch identifier.

6. The apparatus of claim 1 further comprising baffle means in the form of vertically extending plates located within the separator chamber at a position from the vertical line of passage commensurate with restraining lighter particles from returning to the first fraction after separation.

* * * * *